(12) United States Patent
Johnson et al.

(10) Patent No.: US 7,204,245 B2
(45) Date of Patent: *Apr. 17, 2007

(54) AEROSOL ENHANCEMENT DEVICE

(75) Inventors: Robert Johnson, Yucca Valley, CA (US); Robert DuBose, Oakland, OR (US)

(73) Assignee: Clinical Technologies, Inc, Broadview Heights, OH (US)

( * ) Notice: Subject to any disclaimer, the term of this patent is extended or adjusted under 35 U.S.C. 154(b) by 1035 days.

This patent is subject to a terminal disclaimer.

(21) Appl. No.: 09/855,403

(22) Filed: May 15, 2001

(65) Prior Publication Data

US 2002/0121275 A1    Sep. 5, 2002

Related U.S. Application Data (63) Continuation-in-part of application No. 09/610,801, filed on Jul. 6, 2000, now Pat. No. 6,363,932.

(51) Int. Cl.
*A61M 11/00* (2006.01)

(52) U.S. Cl. ............... 128/200.14; 128/205.24

(58) Field of Classification Search ............... 128/200.14–200.24, 203.12, 203.24, 203.26, 128/204.18, 204.21, 205.24, 207.14–207.18, 128/202.27
See application file for complete search history.

(56) References Cited

U.S. PATENT DOCUMENTS

| | | |
|---|---|---|
| 3,762,409 A | 10/1973 | Lester |
| 3,769,973 A | 11/1973 | Esbenshade, Jr. |
| 3,826,255 A | 7/1974 | Havstad et al. |
| 4,007,238 A | 2/1977 | Glenn |
| 4,061,698 A | 12/1977 | Thornwald |
| 4,094,317 A | 6/1978 | Wasnich |
| 4,100,235 A | 7/1978 | Thornwald |
| 4,113,809 A | 9/1978 | Abair et al. |
| 4,210,155 A | 7/1980 | Grimes |
| 4,231,973 A | 11/1980 | Young et al. |
| 4,253,468 A | 3/1981 | Lehmbeck |
| 4,259,951 A | 4/1981 | Chernack et al. |
| 4,268,460 A | 5/1981 | Boiarski et al. |
| 4,396,015 A | 8/1983 | Johnson |
| 4,534,343 A | 8/1985 | Nowacki et al. |
| 4,560,519 A | 12/1985 | Cerny |
| 4,657,007 A | 4/1987 | Carlin et al. |
| 4,660,547 A | 4/1987 | Kremer, Jr. |
| 4,823,784 A | 4/1989 | Bordoni et al. |
| 4,844,512 A * | 7/1989 | Gahwiler ............ 285/39 |

(Continued)

FOREIGN PATENT DOCUMENTS

WO    00/27455    *   5/2000    ............ 128/200.14

*Primary Examiner*—Glenn K. Dawson
(74) *Attorney, Agent, or Firm*—Stout, Uxa, Buyan & Mullins, LLP; Donald E. Stout (57) ABSTRACT

An aerosol medication delivery apparatus includes a fixed volume holding chamber which is constructed to allow for a uniformly mixed, concentrated bolus of medicated aerosol to be delivered with each breath. The device further includes a universal inlet, so that any standard small volume nebulizer, as well as any standard metered dose inhaler (MDI), may be utilized therewith. Also filtration can be added to address contaminated patient air and aerosol. A one-way valve is positioned in the patient mouthpiece, to help control the loss of aerosol, and thereby reduce waste.

24 Claims, 8 Drawing Sheets

U.S. PATENT DOCUMENTS

| | | |
|---|---|---|
| 4,911,157 A | 3/1990 | Miller |
| 4,938,209 A | 7/1990 | Fry |
| 4,951,661 A | 8/1990 | Sladek |
| 5,020,530 A | 6/1991 | Miller |
| RE33,642 E | 7/1991 | Lester |
| 5,027,809 A | 7/1991 | Robinson |
| 5,036,840 A | 8/1991 | Wallace |
| 5,062,419 A | 11/1991 | Rider |
| 5,086,765 A | 2/1992 | Levine |
| 5,096,765 A * | 3/1992 | Barnes ................. 128/200.21 |
| 5,099,833 A | 3/1992 | Michaels |
| 5,170,782 A | 12/1992 | Kocinski |
| 5,178,138 A * | 1/1993 | Walstrom et al. ...... 128/200.23 |
| 5,209,225 A | 5/1993 | Glenn |
| 5,235,969 A | 8/1993 | Bellm |
| 5,241,954 A | 9/1993 | Glenn |
| 5,277,175 A | 1/1994 | Riggs et al. |
| 5,287,847 A | 2/1994 | Piper et al. |
| 5,297,543 A | 3/1994 | Larson et al. |
| 5,299,565 A | 4/1994 | Brown |
| 5,357,945 A | 10/1994 | Messina |
| 5,379,760 A | 1/1995 | Ryder |
| 5,388,571 A | 2/1995 | Roberts et al. |
| 5,396,883 A | 3/1995 | Knupp et al. |
| 5,415,161 A | 5/1995 | Ryder |
| 5,431,154 A | 7/1995 | Seigel et al. |
| 5,458,135 A | 10/1995 | Patton et al. |
| 5,465,712 A * | 11/1995 | Malis et al. ........... 128/205.25 |
| 5,477,849 A | 12/1995 | Fry |
| 5,479,920 A * | 1/1996 | Piper et al. ............ 128/204.23 |
| 5,503,139 A | 4/1996 | McMahon et al. |
| 5,513,626 A | 5/1996 | Hamilton |
| 5,520,167 A | 5/1996 | Hamilton |
| 5,546,930 A | 8/1996 | Wikefeldt |
| 5,570,682 A | 11/1996 | Johnson |
| 5,579,757 A | 12/1996 | McMahon et al. |
| 5,584,285 A | 12/1996 | Salter et al. |
| 5,586,551 A | 12/1996 | Hilliard |
| 5,596,982 A | 1/1997 | Blaha-Schnabel |
| 5,598,835 A | 2/1997 | von Schrader |
| 5,613,489 A | 3/1997 | Miller et al. |
| 5,653,223 A | 8/1997 | Pruitt |
| 5,676,130 A * | 10/1997 | Gupte et al. ........... 128/203.19 |
| 5,685,291 A | 11/1997 | Marsh |
| 5,704,344 A | 1/1998 | Cole |
| 5,727,542 A | 3/1998 | King |
| 5,738,086 A | 4/1998 | McMahon et al. |
| 5,752,502 A | 5/1998 | King |
| 5,775,320 A | 7/1998 | Patton et al. |
| 5,782,232 A | 7/1998 | Rowland |
| 5,797,389 A | 8/1998 | Ryder |
| 5,823,179 A | 10/1998 | Grychowski et al. |
| 5,848,587 A * | 12/1998 | King .................... 128/200.18 |
| 5,988,162 A | 11/1999 | Retallick, III |
| 6,014,972 A | 1/2000 | Sladek |
| 6,026,807 A * | 2/2000 | Puderbaugh et al. ... 128/200.23 |
| 6,085,741 A | 7/2000 | Becker |
| 6,116,233 A | 9/2000 | Denyer et al. |
| 6,123,070 A * | 9/2000 | Bruna et al. ........... 128/203.15 |
| 6,138,668 A | 10/2000 | Patton et al. |
| 6,155,268 A * | 12/2000 | Takeuchi .................... 131/273 |
| 6,176,234 B1 * | 1/2001 | Salter et al. ........... 128/200.18 |
| 6,223,745 B1 | 5/2001 | Hammarlund et al. |
| 6,363,932 B1 * | 4/2002 | Forchione et al. ..... 128/203.12 |
| 6,553,987 B1 * | 4/2003 | Davies ................... 128/200.14 |
| 6,578,571 B1 * | 6/2003 | Watt ...................... 128/200.14 |
| 2003/0015195 A1 * | 1/2003 | Haaije de Boer et al. ..................... 128/203.15 |

* cited by examiner

AEROSOL ENHANCEMENT DEVICE

This application is a continuation-in-part of application Ser. No. 09/610,801, also entitled Aerosol Enhancement Device, filed on Jul. 6, 2000 now U.S. Pat. No. 6,363,932, which is commonly assigned and herein expressly incorporated by reference.

BACKGROUND OF THE INVENTION

This invention relates generally to an improved aerosol inhalation device, and more particularly to an aerosol enhancement device which is usable in combination with both a nebulizer and a metered dose inhaler.

Aerosol inhalation devices, for the purpose of delivering medication, entrained in an aerosol spray, to a patient using inhalation therapy, as an alternative to oral medications such as capsules or pills, or to injected medications, are well known in the art. For example, U.S. Pat. No. 4,210,155 to Grimes is representative of the prior art. In the Grimes patent there is disclosed a fixed volume mist accumulation chamber for use in combination with a nebulizer and a tee connection of an inhalation conduit for accumulating medicated mist and facilitating its delivery to a patient.

However, the Grimes device, as is typical for prior art devices, is plagued with problems typical of such devices. These problems include, for example, nonuniform concentrations of medication, resulting in difficulties in regulating patient dosage, and significant waste of medication. Additionally, the Grimes device is relatively complex, so that it is expensive to manufacture and difficult to use.

Many other such devices are available which do not include a mixing chamber. In other words, the nebulizer is attached directly to the aforementioned tee connection. Of course, such devices are even less suited to satisfactory regulation of the medication being delivered to the patient than the Grimes device, because there is substantially no ability to uniformly mix the medication with entrained fluid, such as air, before delivery to the mouthpiece on which the patient is inhaling.

In addition to nebulizers, metered dose inhalers (MDI) are also available for delivering a medicated aerosol to a patient. These MDI devices differ from nebulizers primarily in that a propellant is used to deliver the medication.

It would be advantageous to have an aerosol medication delivery device which included a mixing chamber between the medication delivery apparatus and the mouthpiece, wherein the medication could be uniformly mixed with entrained air in an improved manner over that achieved by the Grimes patent apparatus. It would also be beneficial for such a device to be simple to manufacture and assemble, and easy to use. Finally, if such a device could be made universally adaptable for use with any known nebulizer on the market, as well as with MDI's, this would be a great advance in the art.

SUMMARY OF THE INVENTION

The present invention provides an aerosol medication delivery apparatus which incorporates the aforementioned advantages. The inventive device includes a fixed volume holding chamber which is constructed to allow for a uniformly mixed, concentrated bolus of medicated aerosol to be delivered with each breath. The device further includes a universal inlet, so that any standard small volume nebulizer, as well as any standard MDI, may be utilized therewith. Also filtration can be added to address contaminated patient air and aerosol. A one-way valve is positioned in the patient mouthpiece, to help control the loss of aerosol, and thereby reduce waste.

More particularly, an aerosol enhancement device is provided which comprises a mouthpiece and a spacer member fluidly attached to the mouthpiece. The spacer member has interior walls which define an interior volume, which comprises a mixing chamber. An inlet port is disposed in the spacer member for receiving a medicated aerosol from an exterior source into the mixing chamber. An air inlet port is disposed in the spacer member, as well, for receiving air into the air passage. Advantageously, the mixing chamber is generally octagonal in configuration, which the inventors have found assists in collecting and refusing excess medication.

In another aspect of the invention, an aerosol enhancement device is provided which comprises a mouthpiece and a spacer member fluidly attached to the mouthpiece. The spacer member is fluidly attached to the mouthpiece via a mouthpiece port, and has an outer body which defines an interior volume. An inlet port is disposed in the spacer member for receiving a medicated aerosol from an exterior source into the interior volume. Advantageously, an adapter is associated with the medicated aerosol inlet port. The inventive adapter comprises a universal fitting which is capable of attaching the spacer member to either a nebulizer or a metered dose inhaler (MDI).

Preferably, the inventive adapter is reversible, being disposable in a first orientation for attachment of the spacer member to a nebulizer, and being disposable in a second orientation for attachment of the spacer member to an MDI. In its preferred configuration, the universal adapter comprises a first rigid connector end and a second flexible connector end, the first rigid connector end being adapted for attachment to a nebulizer and the second flexible connector end being adapted for attachment to an MDI. The adapter preferably further comprises a flange portion for engaging the adapter with the spacer member.

In still another aspect of the invention, an aerosol enhancement device is provided which comprises a mouthpiece having a first port for fluid communication with a patient's mouth, a second port which is open to atmosphere, and a third port, wherein an airway fluidly communicates with each of the first, second, and third ports. A medication dispenser is attached to the third port and a one-way flap valve is disposed in the second port. The one-way flap valve advantageously includes a valve seat for receiving the flap valve and for preventing the flap valve from entering the airway.

In yet another aspect of the invention, a spacer member is provided which is usable with a mouthpiece, for dispensing medicated aerosol to a patient. The inventive spacer member comprises an outer body which defines an interior volume or mixing chamber. An inlet port is disposed in the spacer member for receiving a medicated aerosol from an exterior source into the mixing chamber. An air inlet port is also disposed in the spacer member for receiving air into the mixing chamber. An outlet port is provided for dispensing a mixture of the medicated aerosol and inlet air from the mixing chamber into the mouthpiece. Advantageously, a one-way valve is disposed in the air inlet port, for ensuring that there is no loss of medicated aerosol from the mixing chamber.

The invention, together with additional features and advantages thereof, may best be understood by reference to the following description taken in conjunction with the accompanying illustrative drawing.

DESCRIPTION O

Figure 1:
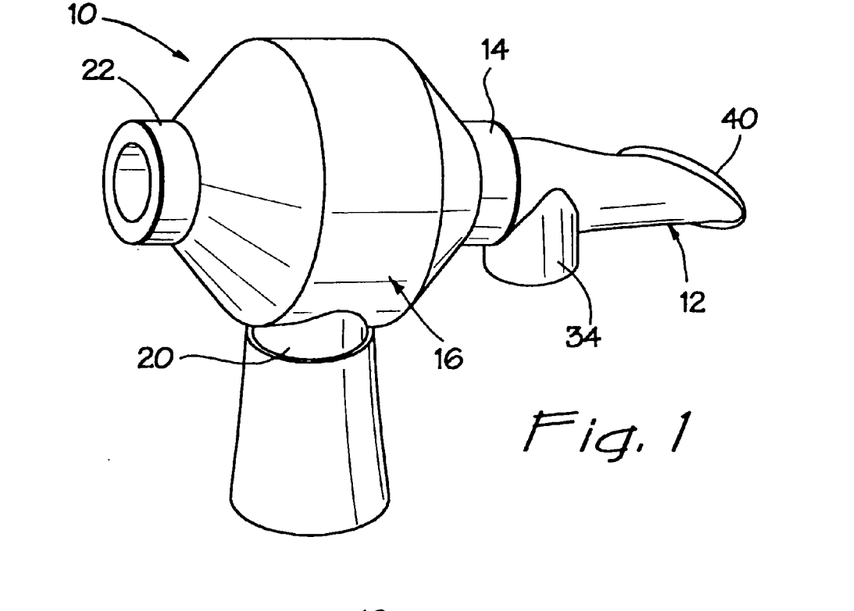
FIG. 1 is a perspective view of an aerosol enhancement device constructed in accordance with the principles of the present invention.
Figure 2:
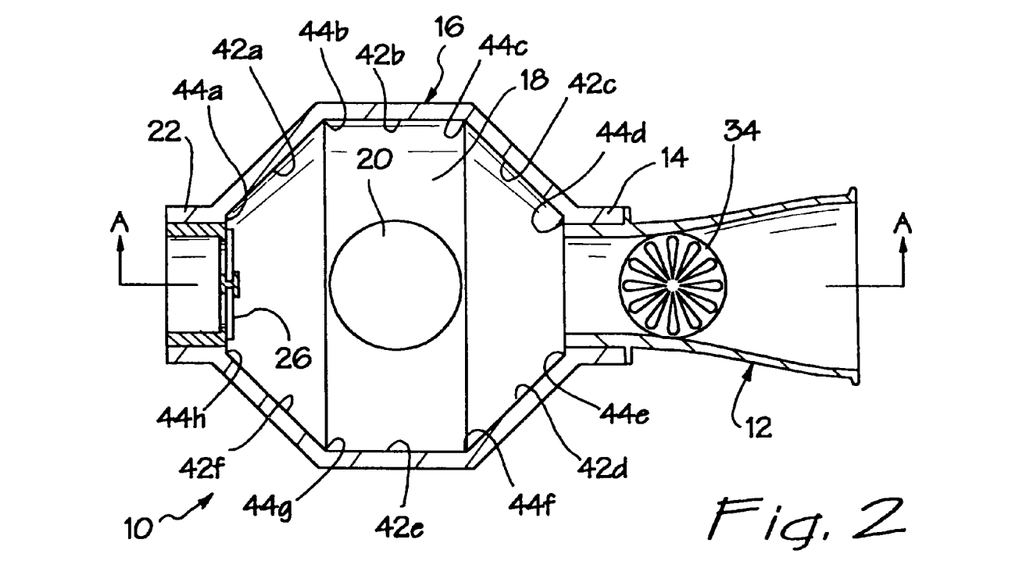
FIG. 2 is a cross-sectional view, taken from the top, of the device shown in FIG. 1.
Figure 3:
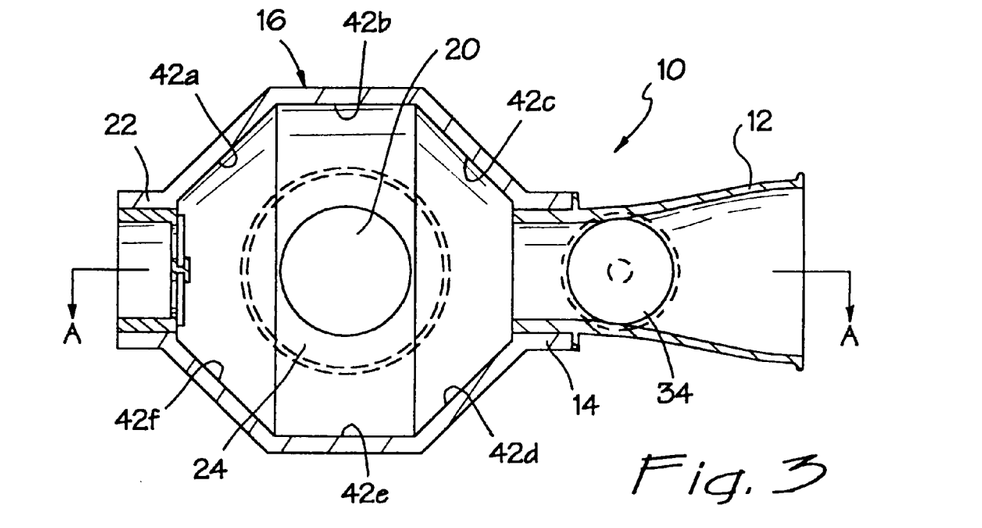
FIG. 3 is a cross-sectional view, taken from the bottom, of the device shown in FIG. 1.
Figure 4:
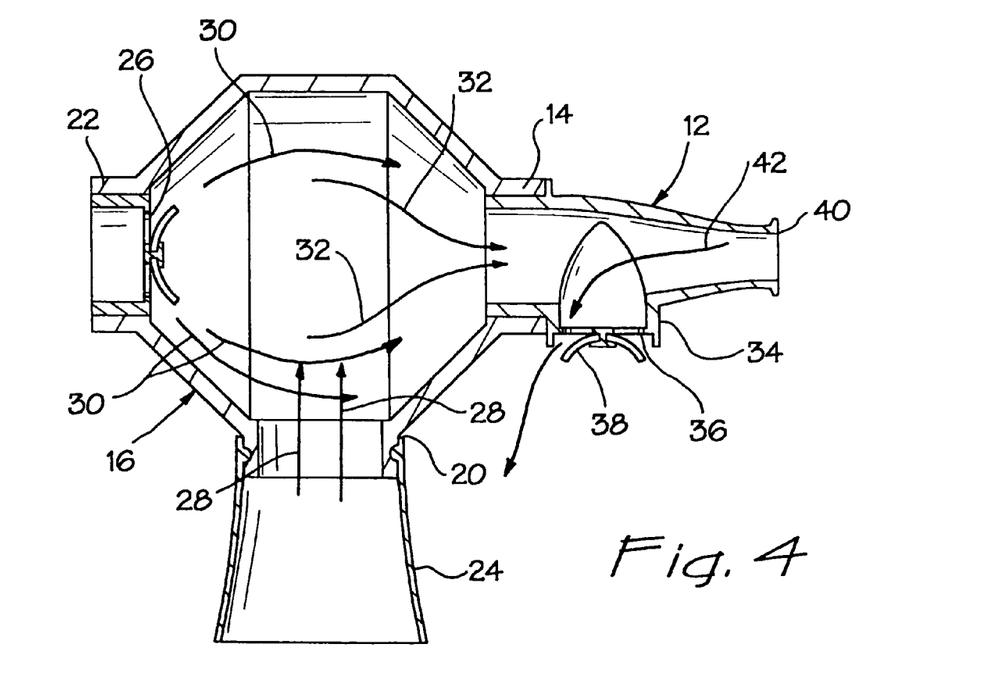
FIG. 4 is a cross-sectional view taken along lines A—A of FIGS. 2 and 3.
Figure 5:
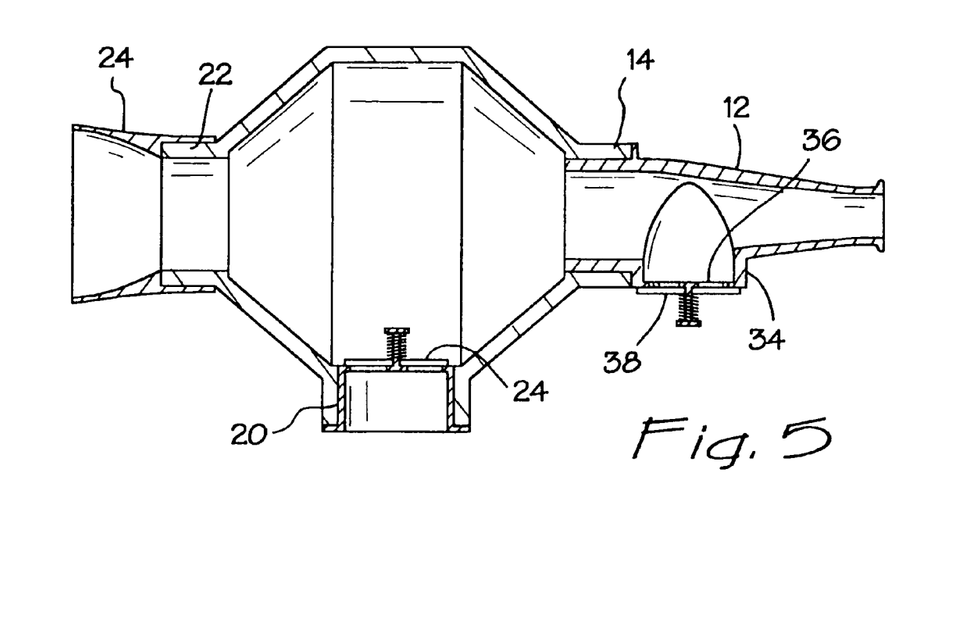
FIG. 5 is a cross-sectional view taken along lines A—A of FIGS. 2 and 3, showing the embodiment of FIG. 1 when it is set-up to function in conjunction with a metered dose inhaler (MDI)
Figure 6:
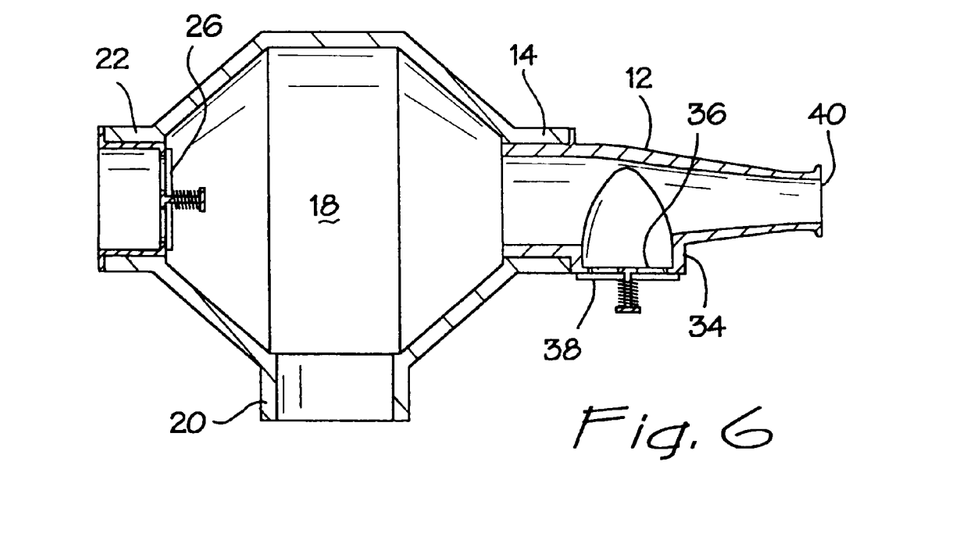
FIG. 6 is a cross-sectional view taken along lines A—A of FIGS. 2 and 3, showing the embodiment of FIG. 1 when it is set-up to function in conjunction with a nebulizer.
Figure 7:
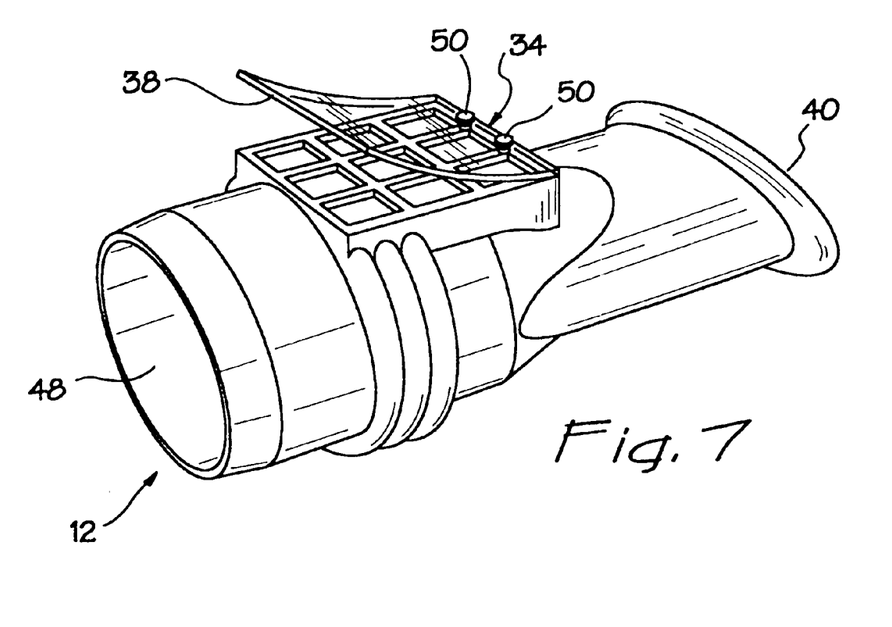
FIG. 7 is a perspective view of a presently preferred embodiment of the mouthpiece portion of the aerosol enhancement device illustrated in FIGS. 1–6.
Figure 8:
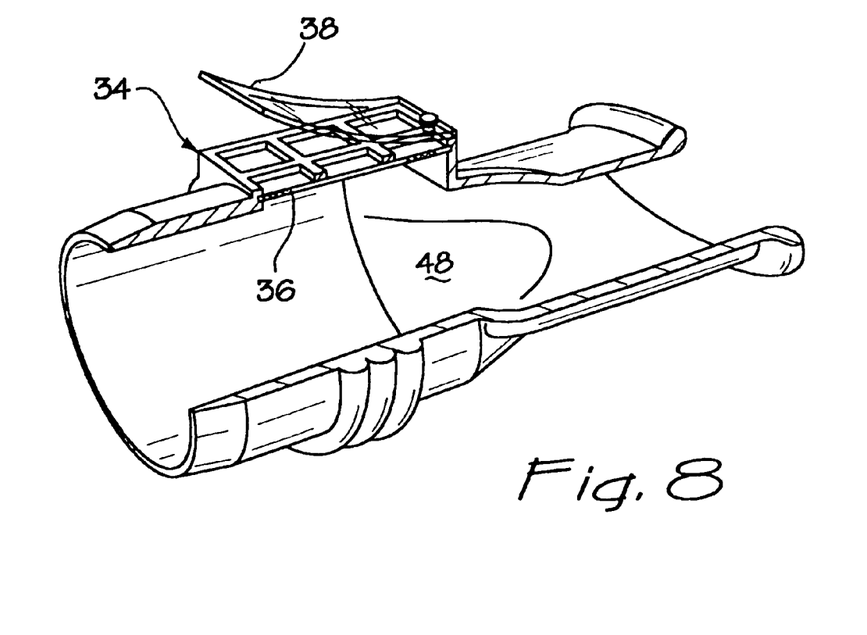
FIG. 8 is a perspective cut-away view of the mouthpiece portion shown in FIG. 7.
Figure 9:
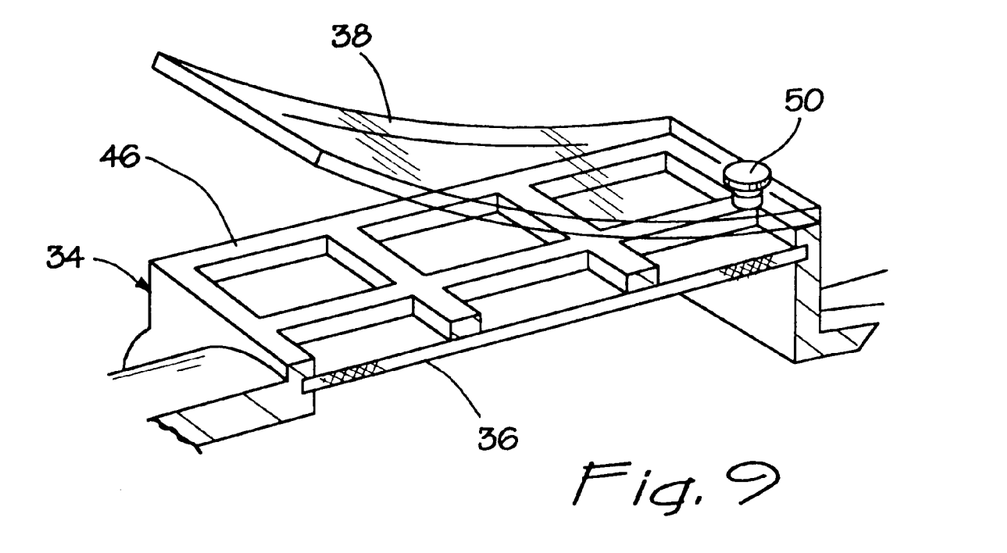
FIG. 9 is an enlarged perspective view of the filter and valve portions of the mouthpiece portion shown in FIGS. 7 and 8.
Figure 10:
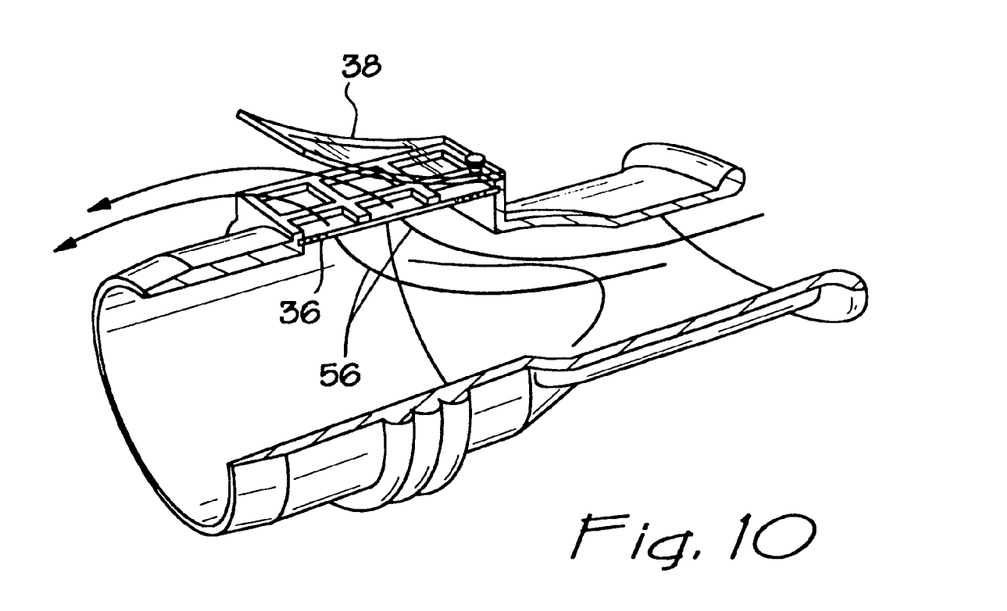
FIG. 10 is a view similar to FIG. 8, illustrating the airflow pattern through the mouthpiece portion during exhalation by a patient using the device.

Advantageously, the mixing chamber 18 in the preferred embodiments is constructed to be defined by interior walls which are arranged to result in a generally octagonal-shaped chamber when viewed in any plane. In other words, the interior wall defining the chamber 18 comprises a plurality of interior generally planar wall segments 42a, 42b, 42c, 42d, 42e, and 42f, for example, which together with the two segments comprising the ports 14 and 22, form the eight generally planar surfaces of the octagon when viewed in cross-section from either the top or the bottom side of the device, as shown in FIGS. 3 and 4, respectively. However, the number of wall segments defining the chamber is not particularly important. Any polygonal shape will suffice, because the key is to have a plurality of corners, or transition zones 44a, 44b, 44c, 44d, 44e, 44f, 44g, and 44h, for example, again as shown in FIGS. 2 and 3, between wall segments and/or ports. In this regard, having eight planar surfaces, as opposed to four, or six, produces substantially better results, as will be described below, with respect to the preservation of medication, because there will be more corners than in a fewer-sided polygon, and thus, greater reduction in wall surface area for a particular volume.

Of course, as is known, the mixing chamber 18 has a function of collecting aerosol distributed from either the nebulizer or MDI, and permitting it to become denser, for supplying an effective amount of medication to the patient. However, sometimes this results in an aerosol mixture which is overly dense, resulting in the wasting of valuable medication, either by over medicating the patient (which may be dangerous as well as wasteful) or by causing the excess medication to merely drain out of the mouthpiece through the exhaust port 34, into the surrounding environment. Advantageously, Applicants have found that the aforementioned corners or angled surfaces, in combination with the plurality of interior wall segments of the polygonal chamber, minimize this waste of medication, by functioning to reduce the interior wall surface area required to define a desired interior volume, and to thereby promote the "raining out" or draining of excess medication within the aerosol mixture to the bottom of the chamber, where it can be collected and reused, before it flows into the mouthpiece.

FIGS. 7–11 illustrate a presently preferred embodiment of the mouthpiece 12 of the inventive aerosol enhancement device 10. In this embodiment, the exhaust port 34 comprises the filter 36, the one-way valve 38, which is in this case a flap valve, and a grid structure 46, which functions as a valve seat when the flap valve is in a closed position, for preventing the valve from descending into the mouthpiece airway 48. A pin or pins 50 are provided to secure one end of the flap valve 38 to the grid structure, in a pivotable manner. The flap valve 38 is preferably made of a pliable medical grade plastic, while the grid structure 46, the remainder of the mouthpiece 12, and the tower or spacer body 16 are all preferably made of a rigid molded plastic, such as ABS, and may be injection molded, if desired.

Figure 11:
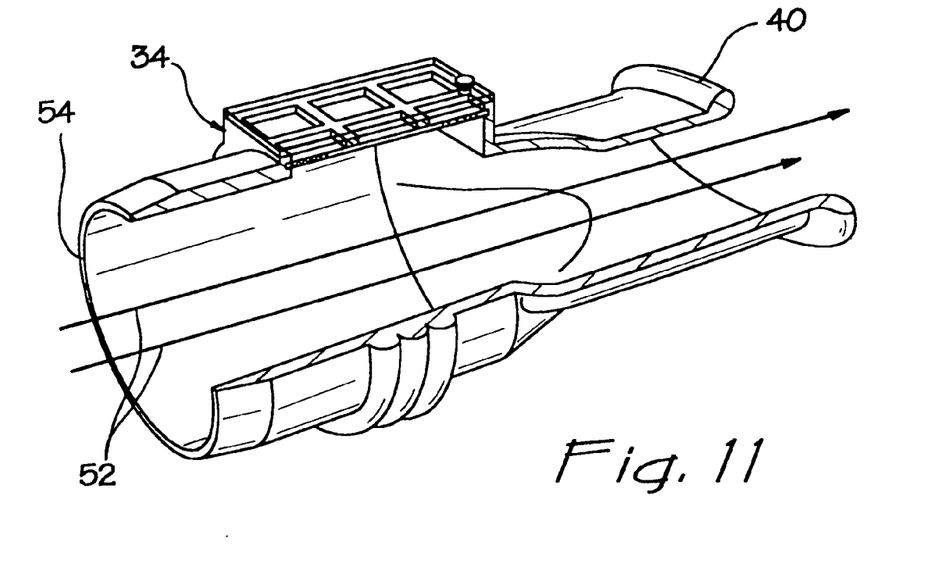
FIG. 11 is a view similar to FIGS. 8 and 10 illustrating the airflow pattern through the mouthpiece portion during inhalation by a patient using the device.

FIG. 11 illustrates the flow of aerosol through the mouthpiece airway 48 during inhalation, which as shown by the arrows 52 is along an axial path therethrough, from the distal end 54, which engages the mouthpiece port 14, to the proximal mouth port 40. The flap valve is closed, as shown, during this cycle. During the exhalation cycle, illustrated in FIG. 10, the exhaled air is directed, as shown by arrows 56, through the exhaust port 34, filter 36, and now-opened flap valve 38.

FIGS. 12–15 illustrate another embodiment of the claimed invention, which is disclosed to emphasize that various arrangements of the components of the inventive device are contemplated within the scope of the invention, and also to illustrate in additional detail the inventive flexible universal boot, or fitting, of the present invention. In this embodiment, like elements are designated by like reference numerals, preceded by the numeral 1. Illustrated is an aerosol enhancement device 110 is similar to that of the device 10 in FIGS. 1–11. However, a generally rectangular tower or spacer body 116 is disclosed, rather than the generally octagonal spacer body 16 of FIGS. 1–11. Applicants believe this to be a less desirable tower body configuration, but it is still potentially viable within the context of the entire inventive concept of Applicants. As in the prior embodiment, this embodiment is useful for a variety of applications, including usage with a nebulizer 158 or MDI 160. Of particular note in FIGS. 12–15 is a more particular illustration of one preferred form of the universal boot or fitting 124 for securing either the nebulizer or MDI, for example, to the spacer body 116. The adaptive fitting 124 includes an engagement flange 162, a rigid connector end 164, and a flexible connector end 166. The flexible connector end 166 is preferably in the nature of a boot, fabricated of a soft pliable material, such as Neoprene, while the engagement flange 162 and rigid connector end 164 are preferably fabricated of a medical grade rigid plastic, such as ABS, which, as discussed above, may be the same material that is used to fabricate the remainder of the device.

Figure 12:
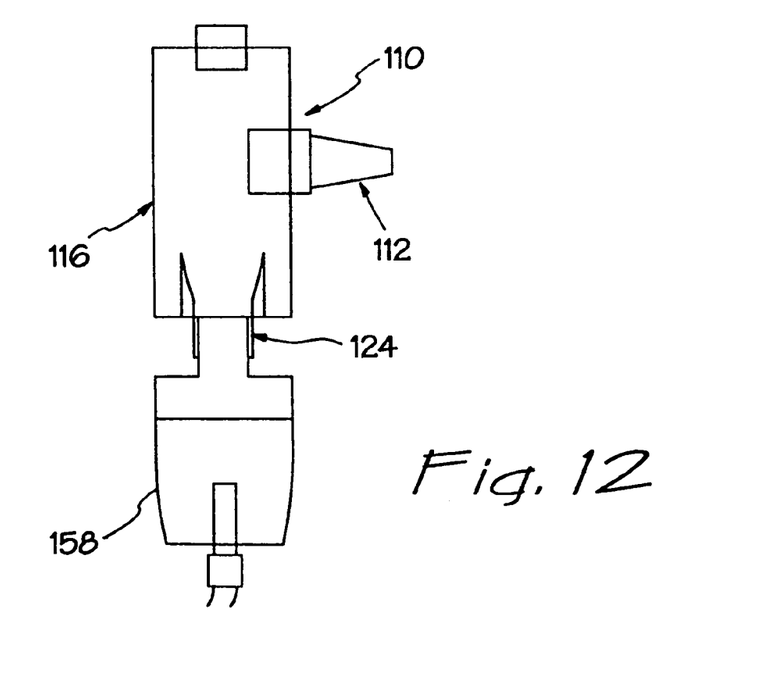
FIG. 12 is a schematic view of an alternative embodiment of the aerosol enhancement device of the present invention, wherein the aerosol enhancement device is configured for use with a nebulizer.
Figure 13:
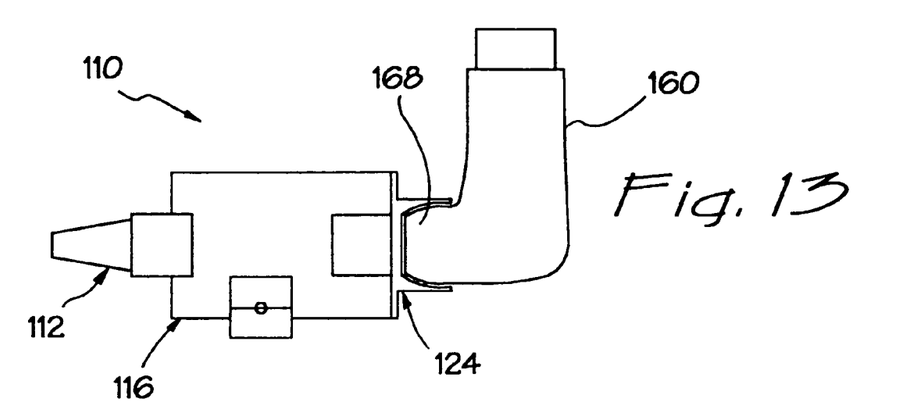
FIG. 13 is a schematic view of the embodiment of FIG. 12, wherein the aerosol enhancement device is configured for use with an MDI.
Figure 14:
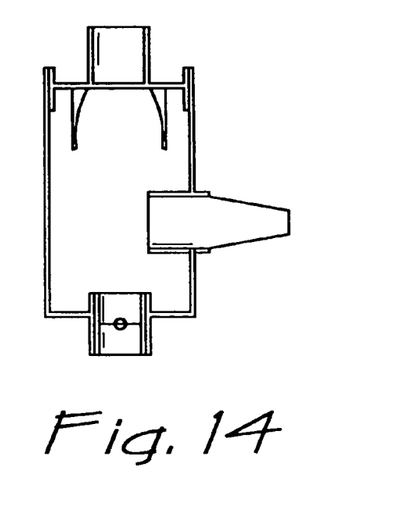
FIG. 14 is a schematic view illustrating, in somewhat greater detail, the structural features of the embodiment shown in FIGS. 12 and 13.
Figure 15:
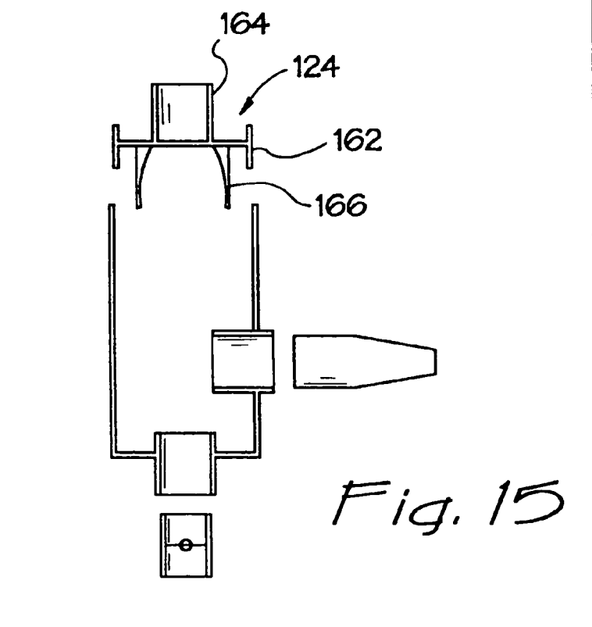
FIG. 15 is an exploded schematic view of the embodiment shown in FIG. 14.

The purpose of the adaptive fitting 124 is to permit the tower body 116 to be able to accommodate attachment of the device to both the nebulizer 158 and the MDI 160, as discussed above. As is shown in FIGS. 12 and 13, the smaller, rigid connector end 164 may be used to attach the device 110 to a nebulizer 158. On the other hand, an MDI typically has a non-round mouthpiece 168, and therefore the inventors have found that a pliable boot connector such as connector 166 is required for a successful fit, by providing a flared access for the MDI boot, as shown in FIG. 13.

Figure 16:
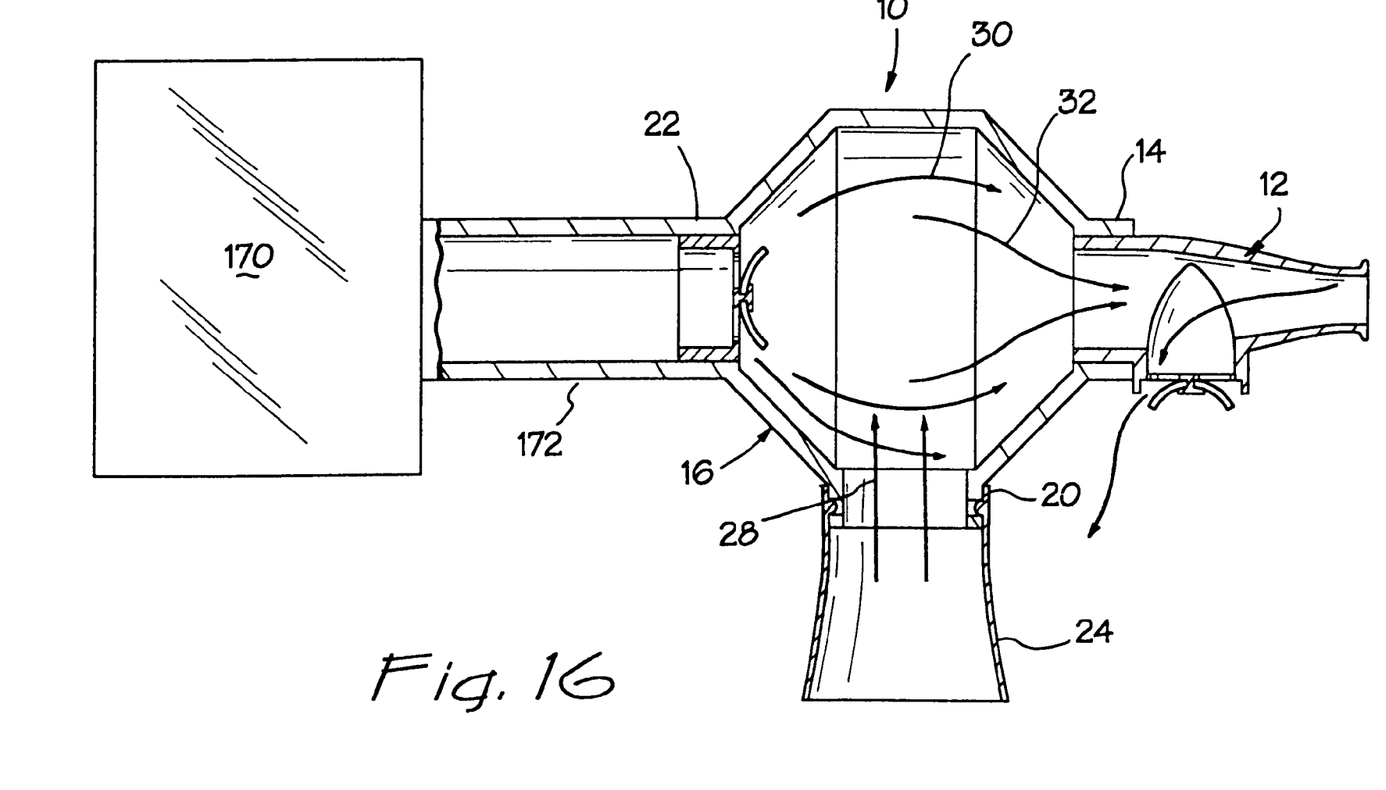
FIG. 16 is a cross-sectional view of an embodiment of the invention, wherein the aerosol enhancement device is disposed in-line in an assisted breathing ventilator system.

FIG. 16 illustrates yet another embodiment of the invention, wherein any of the prior embodiments of the device 10, such as the embodiment shown in FIG. 4, may be installed for use with a ventilator 170, of a type well known for the purpose of providing breathing assistance for patients unable to adequately breathe on their own. Such an installation merely involves attaching the air inlet port 22 (or 20, depending upon the selection of the practitioner) to the ventilator 170, using an air line 172. The inventive aerosol enhancement device 10, 110 otherwise operates in the same manner as above described.

Presently preferred design options include holding chamber volumes ranging from 90 cc to 140 cc, and chamber lengths ranging from 2.95 inches to 1.56 inches, depending upon the chamber volume and the internal diameter of the chamber. The total stacked height of the inventive apparatus, including an attached nebulizer, may range from 6.7 to 8.3 inches in the presently preferred embodiments, depending upon chamber volume and internal diameter.

In operation, in any of the illustrated embodiments, the apparatus 10, 110 is particularly adapted for dual use applications, as noted supra. In particular, the device 10, 110 may be utilized in conjunction with a nebulizer, wherein the tower 16, 116, and in particular, the mixing chamber 18, 118 functions to recirculate medication introduced by the nebulizer, in order to provide a denser application of medication to the patient. The provided fittings are universally suitable for attachment to any known nebulizer. In an alternative configuration, wherein the device 10, 110 is utilized in conjunction with an MDI, the tower 16, 116 functions as a spacer, for the purpose of ensuring a more uniformly mixed dose of medication to the patient.

Whether the device 10, 110 is being used with a nebulizer or an MDI, the purpose of the holding chamber 18, 118 is to repeatedly capture the generated aerosol from the nebulizer or MDI into the fixed volume chamber, which allows for a concentrated bolus of medicated aerosol to be delivered with each breath taken by a patient who is breathing through the mouthpiece 12. In the case of a nebulizer 158, the medicated aerosol is drawn therefrom by the vacuum created by inspiration by the patient through the mouthpiece, while in the case of an MDI, a propellant injects the medicated aerosol therefrom into the chamber 18, 118. Though not shown, in some embodiments, a bridge adapter may be employed to adapt the device to various prior art mouthpieces.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An aerosol enhancement device, comprising:
   a mouthpiece;
   a spacer member fluidly attached to said mouthpiece through a mouthpiece port, said spacer member having interior walls which define an interior volume, said interior volume comprising a mixing chamber;
   an inlet port disposed in said spacer member for receiving a medicated aerosol from an exterior source into said mixing chamber;
   an air inlet port disposed in said spacer member for receiving air into said mixing chamber;
   wherein said interior walls which define said interior volume comprise a plurality of generally planar wall segments and angled transition zones are disposed between adjacent ones of said wall seaments; and
   an adapter disposed in said inlet port for receiving a medicated aerosol, said adapter comprising a universal fitting which is capable of attaching said spacer member to either a nebulizer or a metered dose inhaler (MDI);
   wherein said adapter is reversible, being disposable in a first orientation for attachment of said spacer member to a nebulizer, and being disposable in a second orientation for attachment of said spacer member to an MDI.

2. The aerosol enhancement device as recited in claim 1, and further comprising an exhaust port in said mouthpiece.

3. The aerosol enhancement device as recited in claim 2, and further comprising a one-way valve in said exhaust port.

4. The aerosol enhancement device as recited in claim 3, wherein said one-way valve comprises a flap valve.

5. The aerosol enhancement device as recited in claim 2, and further comprising an exhalation filter in said exhaust port.

6. The aerosol enhancement device as recited in claim 1, and further comprising a one-way valve disposed in said air inlet port.

7. The aerosol enhancement device as recited in claim 1, wherein the inlet port for receiving a medicated aerosol and the air inlet port are interchangeable.

8. The aerosol enhancement device as recited in claim 1, wherein said spacer member comprises eight of said wall segments, such that said mixing chamber is generally octagonal in configuration.

9. An aerosol enhancement device, comprising:
   a mouthpiece;
   a spacer member fluidly attached to said mouthpiece via a mouthpiece port, said spacer member having an outer body which defines an interior volume;
   an inlet port disposed in said spacer member for receiving a medicated aerosol from an exterior source into said interior volume; and
   an adapter associated with said inlet port for receiving a medicated aerosol, said adapter comprising a universal fitting which is capable of attaching said spacer member to either a nebulizer or a metered dose inhaler (MDI);
   wherein said adapter is reversible, being disposable in a first orientation for attachment of said spacer member to a nebulizer, and being disposable in a second orientation for attachment of said spacer member to an MDI;
   said adapter comprising a first rigid Connector end and a second flexible connector end, said first rigid connector end being adapted for attachment to a nebulizer and said second flexible connector end being adapted for attachment to an MDI.

10. The aerosol enhancement device as recited in claim 9, said adapter further comprising a flange portion for engaging said adapter with said spacer member.

11. The aerosol enhancement device as recited in claim 9, and further comprising an air inlet port disposed in said spacer member for receiving air into said air passage.

12. The aerosol enhancement device as recited in claim 9, and further comprising an exhaust port in said mouthpiece.

13. The aerosol enhancement device as recited in claim 12, and further comprising a one-way valve in said exhaust port.

14. The aerosol enhancement device as recited in claim 13, wherein said one-way valve comprises a flap valve.

15. The aerosol enhancement device as recited in claim 12, and further comprising an exhalation filter in said exhaust port.

16. The aerosol enhancement device as recited in claim 11, and further comprising a one-way valve disposed in said air inlet port.

17. The aerosol enhancement device as recited in claim 11, wherein the inlet port for receiving a medicated aerosol and the air inlet port are interchangeable.

18. An aerosol enhancement device, comprising:
    a mouthpiece;
    a spacer member fluidly attached to said mouthpiece through a mouthpiece port, said spacer member having interior walls which define an interior volume, said interior volume comprising a mixing chamber;
    an inlet port disposed in said spacer member for receiving a medicated aerosol from an exterior source into said mixing chamber; and
    an air inlet port disposed in said spacer member for receiving air into said mixing chamber;
    wherein said interior walls defining said interior volume comprise a plurality of generally planar wall segments and angled transition zones are disposed between adjacent ones of said wall segments; and
    wherein the inlet port for receiving a medicated aerosol and the air inlet port are interchangeable.

19. The aerosol enhancement device as recited in claim 18, and further comprising an exhaust port in said mouthpiece.

20. The aerosol enhancement device as recited in claim 19, and further comprising a one-way valve in said exhaust port.

21. The aerosol enhancement device as recited in claim 20, wherein said one-way valve comprises a flap valve.

22. The aerosol enhancement device as recited in claim 19, and further Comprising an exhalation filter in said exhaust port.

23. The aerosol enhancement device as recited in claim 18, and further comprising a One-way valve disposed in said air inlet port.

24. The aerosol enhancement device as recited in claim 18, and further comprising an adapter disposed in said inlet port for receiving a medicated aerosol, said adapter Comprising a universal fitting which is capable of attaching said spacer member to either a nebulizer or a metered dose inhaler (MDI).

* * * * *